(12) United States Patent
Kostrzewski et al.

(10) Patent No.: US 10,705,394 B2
(45) Date of Patent: Jul. 7, 2020

(54) DISPLAY SYSTEM, DEVICE, AND METHOD

(71) Applicant: Physical Optics Corporation, Torrance, CA (US)

(72) Inventors: Andrew Kostrzewski, Garden Grove, CA (US); Kang Lee, Woodland Hills, CA (US); Robert Waldo, Torrance, CA (US); Tomasz Jannson, Torrance, CA (US)

(73) Assignee: PHYSICAL OPTICS CORPORATION, Torrance, CA (US)

( * ) Notice: Subject to any disclaimer, the term of this patent is extended or adjusted under 35 U.S.C. 154(b) by 161 days.

(21) Appl. No.: 15/488,286

(22) Filed: Apr. 14, 2017

(65) Prior Publication Data

US 2017/0363925 A1 Dec. 21, 2017

Related U.S. Application Data

(60) Provisional application No. 62/350,585, filed on Jun. 15, 2016.

(51) Int. Cl.
| | |
|---|---|
| *G02F 1/1362* | (2006.01) |
| *G02F 1/1335* | (2006.01) |
| *G02F 1/13357* | (2006.01) |
| *B64D 43/00* | (2006.01) |
| *G06F 1/16* | (2006.01) |
| *B60K 35/00* | (2006.01) |

(52) U.S. Cl.
CPC ........ *G02F 1/136286* (2013.01); *B60K 35/00* (2013.01); *B64D 43/00* (2013.01); *G02F 1/1335* (2013.01); *G02F 1/1336* (2013.01); *G02F 1/133504* (2013.01); *G06F 1/1637* (2013.01); *B60K 2370/20* (2019.05); *B60K 2370/33* (2019.05); *B60K 2370/345* (2019.05); *B60K 2370/349* (2019.05); *B60K 2370/81* (2019.05); *B60K 2370/828* (2019.05)

(58) Field of Classification Search
CPC ............ G02F 1/136286; G02F 1/1336; G02F 1/133504; G02F 1/1335; B64D 43/00; G06F 1/1637; B60K 2370/828; B60K 2370/81; B60K 2370/345; B60K 2370/20; B60K 2370/349; B60K 2370/33
USPC .................................................. 349/149, 152
See application file for complete search history.

(56) References Cited

U.S. PATENT DOCUMENTS

| | | | | |
|---|---|---|---|---|
| 2004/0095255 | A1* | 5/2004 | Namaky | ............ B60R 16/0315 340/815.78 |
| 2006/0164261 | A1* | 7/2006 | Stiffler | ................... G01C 23/00 340/945 |
| 2010/0014313 | A1* | 1/2010 | Tillin | ................. G02B 27/0101 362/606 |

* cited by examiner

*Primary Examiner* — Charles S Chang
(74) *Attorney, Agent, or Firm* — Sheppard, Mullin, Richter & Hampton LLP

(57) ABSTRACT

An assembly and method for updating a display assembly of a control panel is disclosed with optimal uniform illumination. In some instances, embodiments include efficient and cost effective methods for upgrading display assemblies without having to completely overhaul the electrical, mechanical, or wiring components already existing within the control panel.

14 Claims, 9 Drawing Sheets

DISPLAY SYSTEM, DEVICE, AND METHOD

CROSS-REFERENCE TO RELATED APPLICATIONS

This application claims the benefit of U.S. Provisional Application No. 62/350,585 filed on Jun. 15, 2016, which is incorporated herein by reference in its entirety.

TECHNICAL FIELD

The present technology relates generally to replaceable units for electrical and mechanical platforms, and more particularly, relates to retrofitting hardware onto pre-existing electrical and mechanical platforms for the purpose of enabling an enhanced visual display to the user.

BACKGROUND

The cockpit or information display area presents the necessary information that allows the pilot or driver to take control of the immediate airplane, ship or vehicle. Often, the cockpit or information display area may include a set or arrangement of information systems that displays different types of information, such as control heading, speed, altitude, vertical navigation, lateral navigation, wind speed, fuel temperature, flight plan, speed control, navigation control and the like.

Older airplanes, ships or vehicles often have outdated information systems as they present information in analog format via non-digital displays, such as gauges and meters. However, there may be a preference to have such information presented in digital format, especially when considering accuracy, power conservation, eliminating observational error and information storage concerns. However, the digital optimization of a cockpit or information display area can be expensive and complex if the entire information system is completely overhauled without utilizing any of the original parts, such as the electrical, mechanical and wiring components. As such, there is a need to upgrade and digitally optimize outdated information systems of operational platforms in a cost-effective manner without having to eliminate the entire outdated information system.

BRIEF SUMMARY OF EMBODIMENTS

According to various embodiments of the disclosed technology, disclosed is a method for updating a display assembly of a control panel that includes removing a non-electronic display panel from the control panel, where the internal wirings initially connected to a non-digital display still remain within the control panel. The method may also include installing a new electronic display panel with a front end and a back end onto a surface of the control panel and coupling an electronic module that was once connected to the non-digital display to the back end of the new electronic display panel. The front end of the digital display may be installed to be aligned with a surface plane of the control panel with the back end of the new electronic display panel connected to the already existent internal writings of the electronic module so that internal wirings within the control panel remain invariant even when updating the control panel to include the new electronic display panel.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

The following description is not to be taken in a limiting sense, but is made merely for the purpose of describing the general principles of the disclosed embodiments. The present embodiments address the problems described in the background while also addressing other additional problems as will be seen from the following detailed description. Numerous specific details are set forth to provide a full understanding of various aspects of the subject disclosure. It will be apparent, however, to one ordinarily skilled in the art that various aspects of the subject disclosure may be practiced without some of these specific details. In other instances, well-known structures and techniques have not been shown in detail to avoid unnecessarily obscuring the subject disclosure.

Some embodiments of the disclosure provide a display assembly to be installed or retrofitted onto an existing control panel. Such control panels may include an instrument board or dashboard with one or more display panels that display information and control features that enable the viewer to effectively control the operational platform. By way of example only, the operational platform may be an aircraft, a ground vehicle, spaceship, watercraft, and other manned or unmanned platforms.

In some embodiments, the display assembly includes an electronic display, where the electronic display is connected to an electronic module so that digital information is displayed on the electronic display using optoelectronic applications. By way of example, the electronic module may include the original and already existing electrical wirings already contained within its operational platform. As such, in some instances, the original writings of the electronic module may be connected to a modern or new electronic display. Additionally, this further allows the rearrangement of how information may be displayed to the pilot or user without having to overhaul the entire existing electronic module or wirings already contained within the operational platform.

Figure 1:
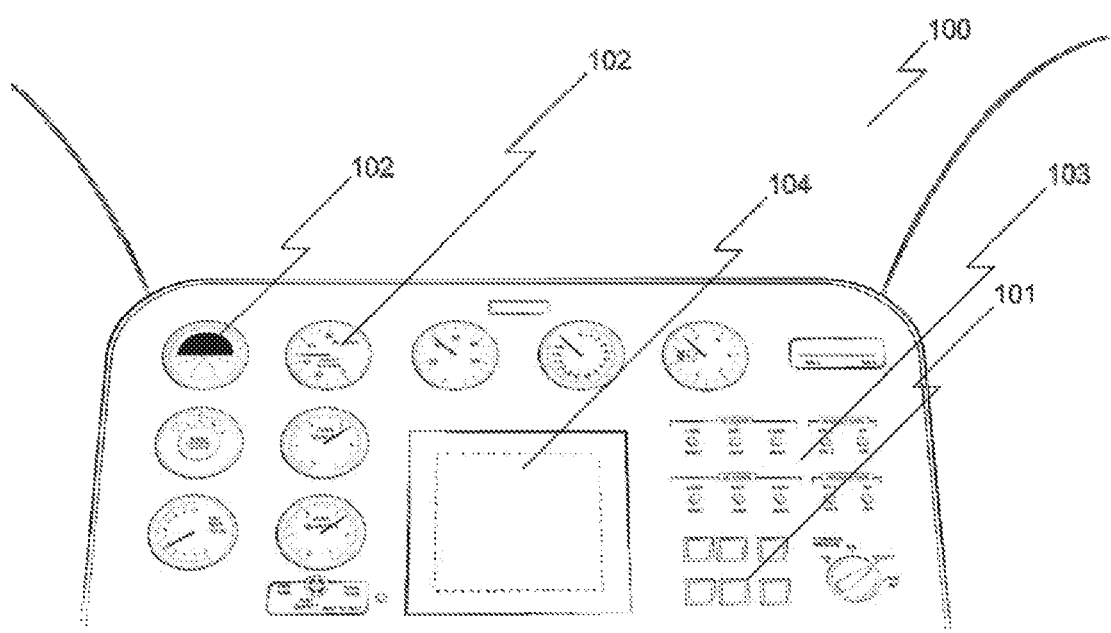
FIG. 1 illustrates a control panel of an operational platform with an electronic display panel according to one embodiment.

FIG. 1 illustrates a control panel 100 of an operational platform with an electronic display panel 104 according to one embodiment. As depicted, the control panel 100 may also include a plurality of analog and non-digital display component, such as buttons 101, gauges 102 and switches 103 that display information and provide control mechanisms. However, as briefly discussed above, there may be a need to update the non-digital display components to transmit digital information, especially when considering accuracy, power conservation, eliminating observational error and information storage concerns. As such, some or all of the non-digital display components may be updated so that an electronic display panel 104 may be installed, thus making it easier for the pilot or viewer to quickly and easily observe the displayed information. In some instances, the electronic display panel 104 may be a Liquid Crystal Display (hereinafter "LCD") panel.

As illustrated, FIG. 1 shows the installation of an electronic display panel 104, as the electronic display panel 104 is retrofitted onto the control panel 100 to now replace what was once a non-digital display component 101, 102, 103. In some instances, all non-digital display components 101, 102, 103 may be modified to display information digitally via an electronic display panel 104. However, in other instances, select non-digital display components 101, 102, 103 may remain so that the control panel 100 displays both digital and analog forms of information. Therefore, by removing the non-digital display component 101, 102, 103, the space and area remaining may be used to retrofit an electronic display with the same size and dimensions of its non-digital display component 101, 102, 103 counterpart.

Figure 2:
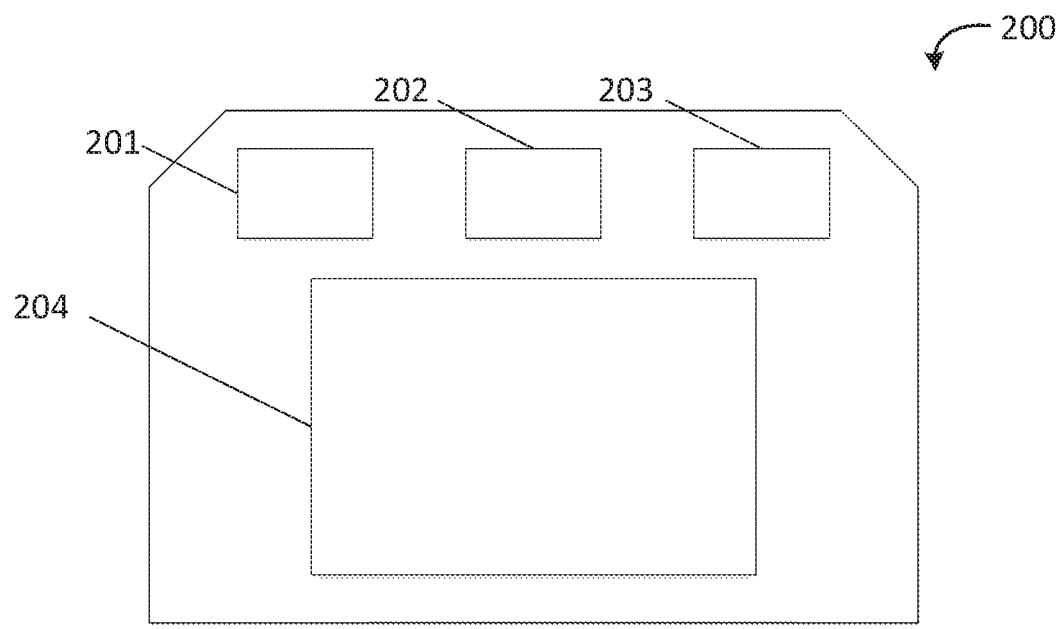
FIG. 2 illustrates a control panel of an operation platform with an electronic display panel according to one embodiment.

FIG. 2 illustrates a control panel 200 of an operation platform with a plurality of electronic display panels 201, 202, 203, 204 according to one embodiment. In this particular example, each and every panel of non-digital display component (not shown here) has already been removed so that the associated data from the removed panels are configured to display information digitally via electronic display panels 201, 202, 203, 204. As such, the pilot or viewer now sees all information displayed on the control panel 200 in a digital format. However, as described in FIG. 1, the information displayed on the control panel 200 may include both digital and analog forms of information.

Figure 3:
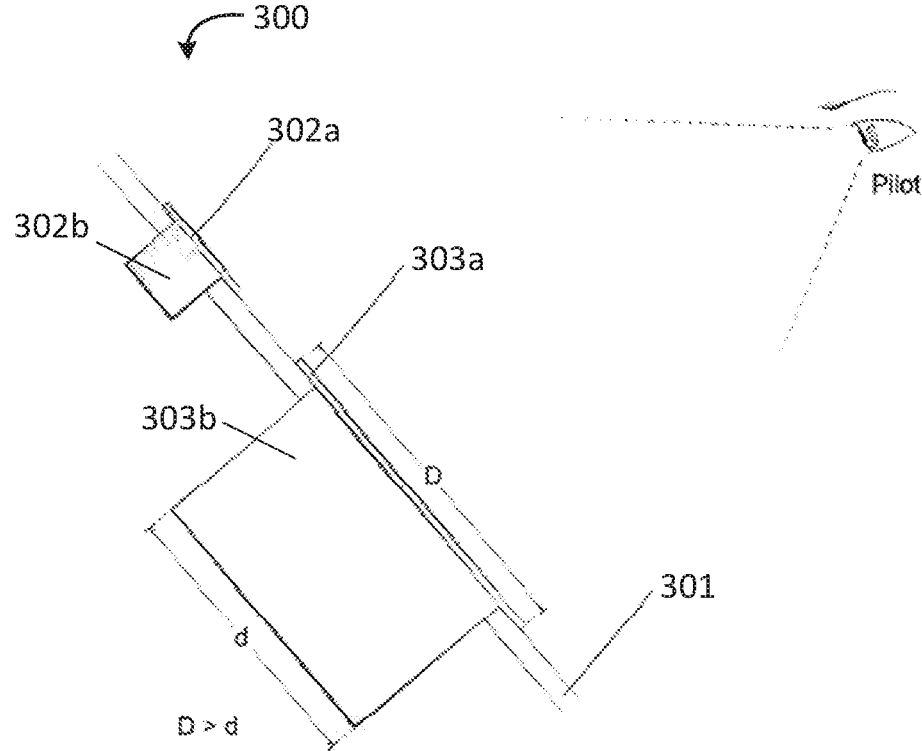
FIG. 3 illustrates a side view of a control panel of an operation platform with an electronic display panel according to one embodiment.

FIG. 3 illustrates a side view of a control panel 300 of an operation platform with electronic display panels 302a, 302b according to one embodiment. Here, FIG. 3 shows how certain components may be modified to present information digitally. For example, the non-digital display components may have been replaced to now include an electronic display panel 302a, 302b. Additionally, behind each newly installed electronic display panel 302a, 302b is the original electronic module 302b, 303b, which may have been the exact same electronic module 302b, 303b used in connection with the non-digital display panel component. Thus the electronic module 302b, 303b of the non-digital display components may be recycled and modified by using its same wires and connecting onto the electronic display panel 302a, 302b to then display digital information.

By way of example only, the electronic assembly units may be "line-replaceable units" (LRU), which are modular components of an airplane, or any other operational platform. The LRU may be configured so that the electronic assembly units may be quickly installed or retrofitted at any operating location without the need to overhaul the operational platforms already existing wiring.

As further depicted, the electronic module 302b, 303b may be fitted within its determined aperture or opening. By way of example, the length and width of the aperture or opening may be identical to the length and width of the corresponding already existing electronic module 302b, 303b, thus allowing the electronic module 302b, 303b to be securely positioned within the control panel. As illustrated, the electronic module 302b, 303b may be placed immediately behind the electronic display panel 302a, 303a, so that each electronic module 302a, 302b is connected to its own electronic display panel 302a, 303a. This may easily allow the retrofitting of electronic modules 302b, 303b, such that the electronic modules 302b, 303b may be easily replaced and modified as needed without disrupting the other electrical and mechanical components of the other electronic modules 302b, 303b and electronic display panels 302a, 303a.

In some instances, the electronic display panels 302a, 303a may be positioned to be fitted or positioned against the top surface of the control panel 301. As depicted, the surface plane of the electronic display panel 302a, 303a may be aligned to be on the same surface plane as the control panel 301. In some instances, the electronic display panels 302a, 303a may have a width dimension of D and the aperture or opening that the electronic display panels 302a, 303a covers may have a width dimension of d, where D is greater than d. In such instances, the area of the electronic display panels 302a, 303a is greater than the aperture or opening.

Figure 4:
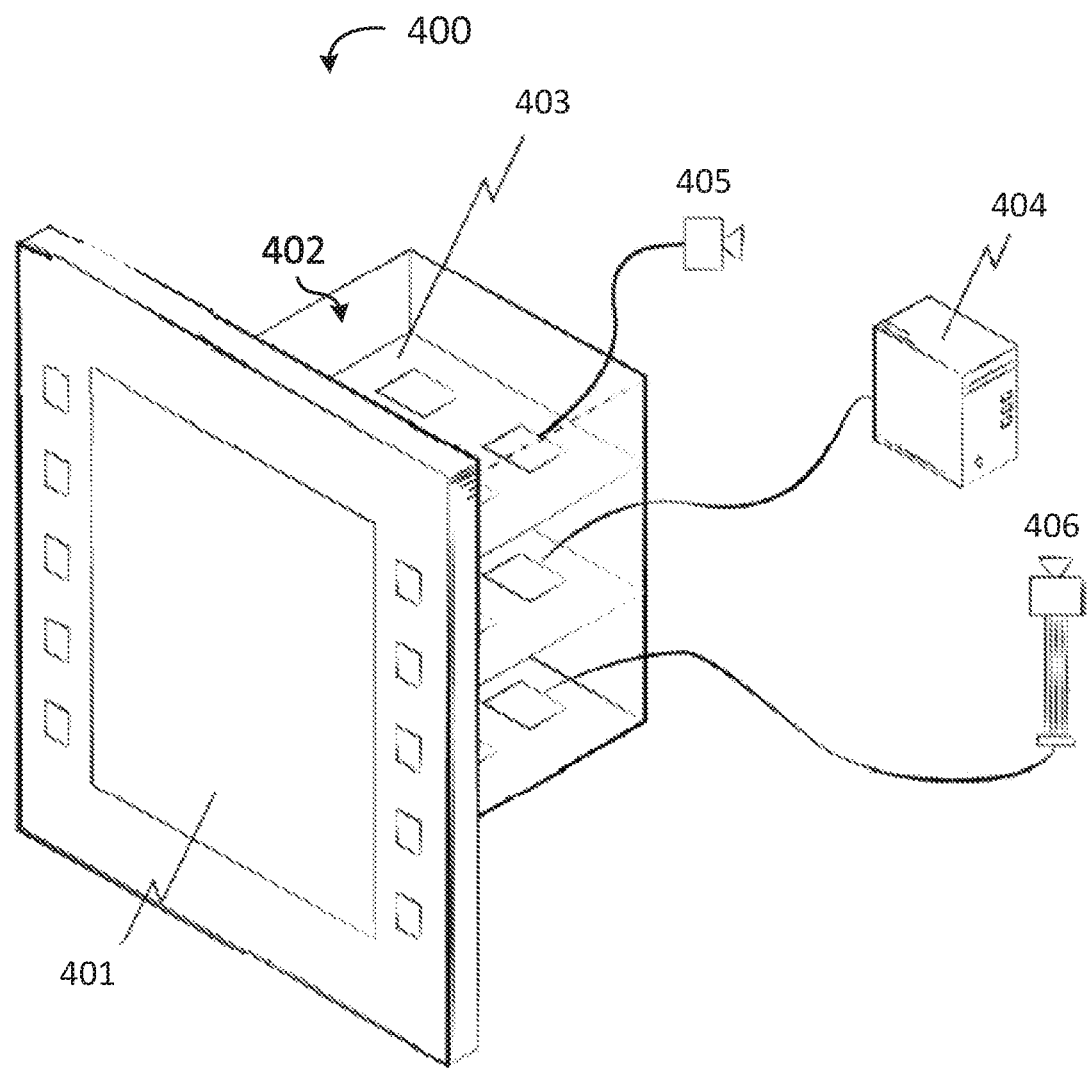
FIG. 4 illustrates a display assembly with an electronic display panel connected to an electronic module according to one embodiment.

FIG. 4 illustrates a display assembly 400 with an electronic display panel 401 and electronic module 402. In some instances, the electronic module 402 may contain a plurality of different electrical hardware, or otherwise known as electronic assembly units 403, 404, 405, 406 to be individually connected or detached from the display electronic unit 402. Thus, a pilot or viewer may actively select the particular electronic assembly units 403, 404, 405, 406 to be included onto the electronic module 402 depending on the type of information the pilot or viewer wishes to see on the control panel. For example, some of the electrical hardware that may be fitted or retrofitted onto the display electronic unit 402 may include a charge coupled device camera 403, mission processor unit 404, loading and storage element 405, data transfer element 406, and the like. Because these individual electronic assembly units 403, 404, 405, 406 may be easily retrofitted onto the display electronic unit 402, this allows for various and specific electronic assembly units 403, 404, 405, 406 to be in communication and integrated onto preexisting platforms.

Each of the electronic assembly units 403, 404, 405, 406 may be connected to the electronic display panel 401 via internal wires so that the digital signals from the electronic assembly units 403, 404, 405, 406 are relayed to the electronic display panel 401. In some instances, the internal wires may be existing wires that were already contained within the operational platform and were attached to the already existing individual electronic assembly units 403, 404, 405, 406. In such cases, the already existing internal wirings may then used to attach onto the newly installed electronic display panel 401 so that the already existent electronic assembly units that were not displaying information digitally to the user, is now displayed in such a manner. In other words, where the original internal wires are used to establish a connection with the electronic display panel 401, the internal wire volume remains invariant when installing one or more electronic display panels 401. This ensures that the removal of old analog system and upgrading to electronic displays can be done without increasing wiring complexity and weight. This further allows for the retrofitting or updating old information systems at a relatively low cost without the need to completely overhaul the entire information system.

Additionally, the display assembly 400 may be a multi-function display. The one or more display panels 401 in this particular example may display information with multiple soft keys that can be used to display information to the user, such as a pilot in a military or commercial aircraft. Furthermore, the multi-function display may include weapons replaceable assemblies (WRA), or otherwise referred to as replaceable units. However, as used herein, the term WRA will be used to refer to any replaceable module component of a platform, whether or not it is a weapons system. Accordingly, typical WRAs include Flight Data Recorders (FDR), Removable Memory Units (RMU), Terrain Awareness Avoidance Units (TAWS), Mission Data Loaders (MDL), Data Loaders (DL), Data Recorders (DR), Audio/Video Recorders (AVR), Data Transfer Units (DTU), Data Transfer Devices (DTD), map storage devices, collision avoidance systems, crash survivable data recorders, and many others. The above WRAs create a non-exclusive, non-complete and possibly-overlapping set, and are given simply for reference.

Figure 5A:
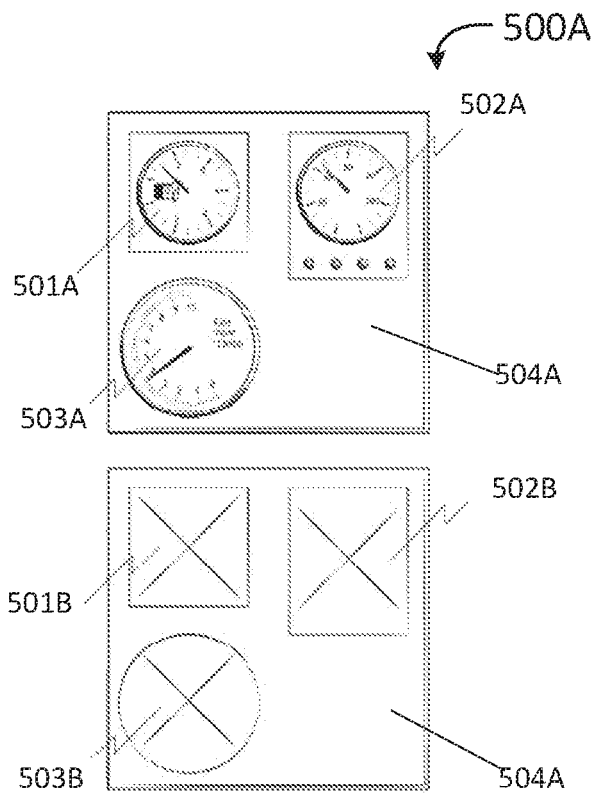
FIG. 5A illustrates a front view of a display assembly according to one embodiment.
Figure 5B:
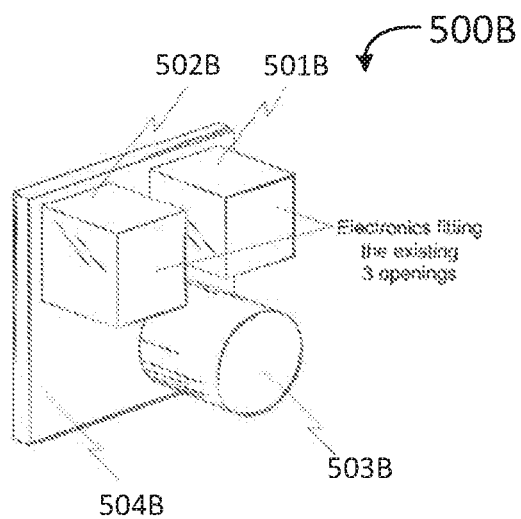
FIG. 5B illustrates a back perspective view of electronic modules according to one embodiment.

FIG. 5A illustrates a front view of a display assembly 500A with a plurality of display panels 501A, 502A, 503A according to one embodiment. The control panel 504A may have apertures or openings 501A, 502A, 503A. As disclosed in FIG. 5B, which is a rear view of the display assembly 500A, electronic assembly units may be placed within those aperture or openings 501A, 502A, 503A as depicted in FIG. 5A. Because FIGS. 5A and 5B illustrate the same display assembly with 5A depicting the front view and 5B depicting the rear view, both FIGS. 5A and 5B will be explained herein together.

In accordance with this particular example, three individual electronic display panels (not shown here) may be installed to lay over the electronic assembly units over each of the apertures or openings 501A, 502A, 503A. In some instances, the surface area of the electronic display panel s may be greater than the area of the aperture or openings 501A, 502A, 503A that will include the electronic modules 501B, 502B, 503B.

Additionally, FIG. 5A illustrates a display assembly with a plurality of display panels 501A, 501B that are in analog and non-digital format. By way of example only, a control panel, such as an aerial cockpit or dashboard, may include one or more analog display panels 501, 502, such as with the use of meters and gauges. Because if such information presented on the meters and gauges are represented digitally, the information may be transferred, processed, and even stored digitally, which are features and characteristics that cannot be performed by analog display. As such, in the event that digital information is to be presented, a processor may be present and connected to a bus that transfers data of all of the connected electronic assembly units to the processor. The bus may then be used as a communication channel amongst the electronic assembly units to provide high flexibility and build a data network from the data collected and generated form the electronic assembly units. By way of example only, the input end of the bus may be customizable, so that the electronic assembly units may be easily replaced with other types depending on the type of information that needs to be presented on the display panels 501A, 501B. The bus may be further customizable so that it can utilize both analog and digital signals.

In some instances, one large electronic display panel (not shown here) may be used to cover the entire available aperture or openings 501A, 502A, 503A present. Additionally, because the installed electronic display panel is to be placed on top of the control panel 504A, the one or more electronic display panels may be used to cover the one or more aperture or openings 501A, 502A, 503A.

Figure 6:
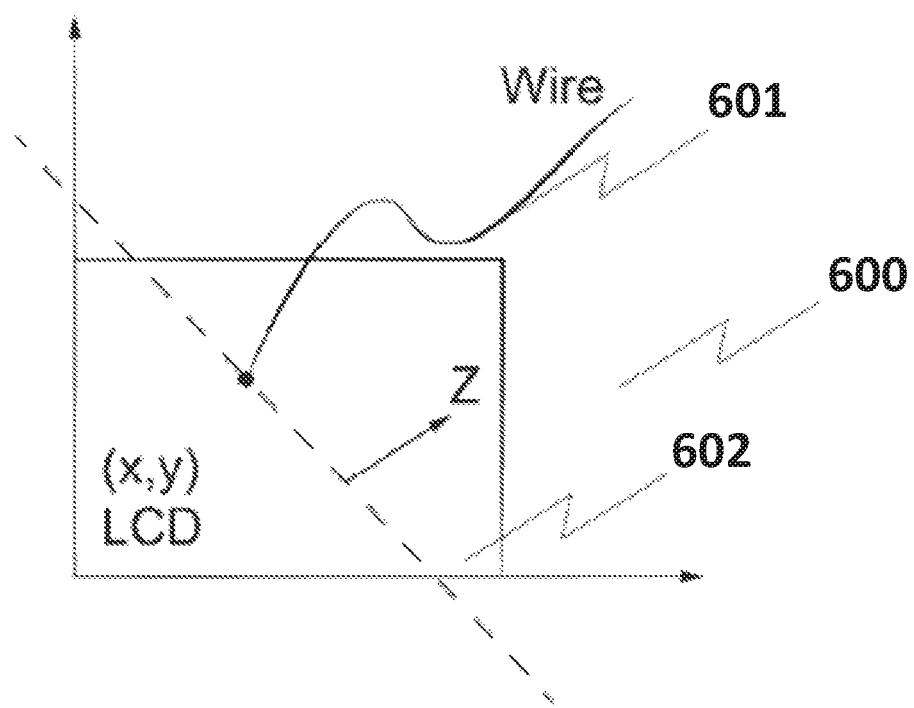
FIG. 6 illustrates a graphical representation of installed internal wirings for a display assembly according to one embodiment.

FIG. 6 illustrates a graphical representation of installed wirings for a display assembly according to one embodiment. FIG. 6 illustrates a graphical representation of a wiring for a display assembly 600 according to one embodiment. Here, the figure illustrates a general function off (x, y, $z_i$, t) where f (x, y, $z_i$) is a display function for the $i^{th}$ display panel, as more than one display panel may be configured onto the control panel. Additionally, $x_i(t)$, $y_i(t)$ is a wired signal function over time, t, for the $i^{th}$ display. As a result, the display assembly 600 with a plurality of electronic assembly units on an existing display electronic unit may be installed, thus avoiding traditional constraints of fixed display panels that displays fixed information. In other words, the display assembly 600 is not directly dependent on the specific history of the various internal wirings 601, but rather though the general specification constraints of the electronic display panel. This is because the electronic modules may be connected or unconnected to a LCD display panel 602. The LCD display panel 602 may be configured with an electrical internal wiring 601 to connect the LCD display panel 602 to the electronic module. Thus, a plurality of separate electronic modules may be individually connected to the LCD display panel 602, allowing for different and varied information to be displayed on the LCD display panel 602. In some instances, more than one electronic modules may be connected to the same LCD display panel 602, thus giving architectural versatility to the control panel or information display area without having to significantly overhaul or modify the core system components of the control panel. However, it should be noted that the LCD display panel 602 may include other display panel types, such as cathode ray tube display, plasma display, and organic light emitting diode device by way of example only.

Figure 7:
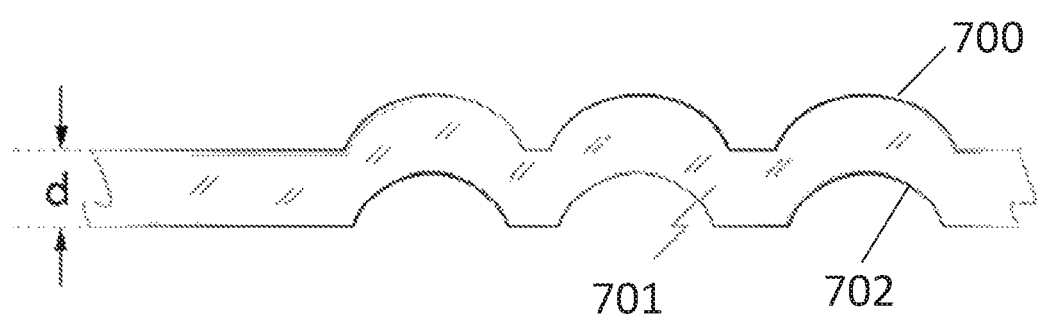
FIG. 7 illustrates a diffuser sheet with a focusing lens for the electronic display panel according to one embodiment

FIG. 7 illustrates a diffuser sheet 701 with a focusing lens 700, 702 for the display panel in the display assembly according to one embodiment. Where the display panel is an LED panel, a backlight unit is placed behind the LCD panel as a light source. A backlight unit is required because LCDs do not produce light by themselves and requires a light source to produce a visible image on the display panel. As such, the backlight units may illuminate the LCD from the side or back of the display panel. In some instances, the backlight unit may include a collimator immediately in front of the backlight unit, which may be a illumination matrix unit. Furthermore, the illumination matrix unit may include LCDs in some instances. A collimator takes the light rays from the backlight unit and configures the light rays to be parallel with one another, resulting in a minimal spreading of the light beams as the light beams propagate.

In some embodiments, the light source from the backlight of the LCD may also be passed through a diffuser 701, which may further provide a greater degree of light distribution and intensity. Thus, the diffuser 701 can spread light evenly across a surface, and further minimize or remove high intensity bright spots to help provide a uniform illumination on the display panel.

Dual focusing lens 700, 702 may be placed on opposite ends of the diffuser 701. The dual focusing lens may further focus the collimated ray bundles. The total focusing power of the dual focusing lens 700, 702 may depend on the distance, d, between the dual focusing lens 700, 702. A closer distance between the two focusing lens 700, 702 results in a higher total focusing power while a further distance apart between the two focusing lens 700, 702 results in a lower total focusing power. Thus, the focusing power may be adjusted with the distance, d, of the two focusing lens 700, 702.

Figure 8:
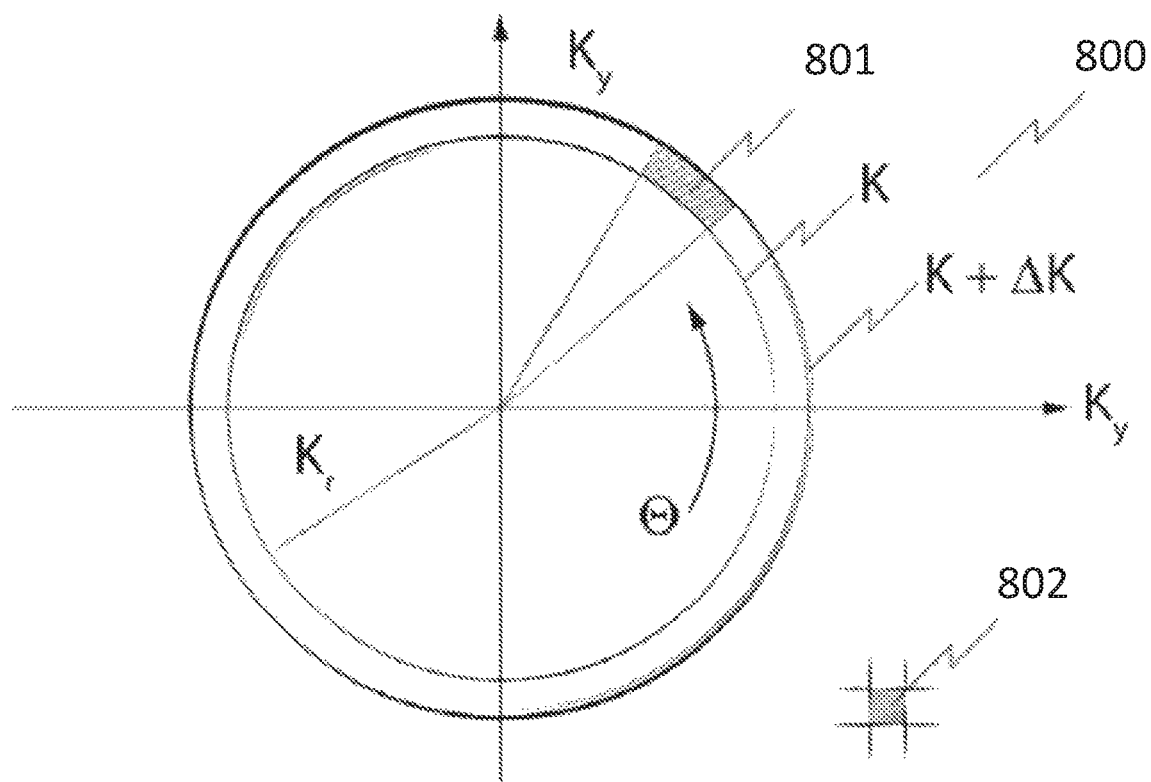
FIG. 8 illustrates a comparison of phase space and angular space when ray tracing light rays of the display panel according to one embodiment.

FIG. 8 illustrates a comparison of performing a ray tracing model 800 of the light ray bundles coming from the light source in phase space 802 and angular space 801 according to one embodiment. The purpose of ray tracing is to provide a detailed prediction of an optical performance of a light source in a display panel for enhanced optical performance. Where the display panel is a LCD panel with a backlight unit, the ray tracing is performed on the light rays emitted from the backlight unit. The optical performance is characterized quantitatively as a function of parameters that are defined to model the structure and properties of the of the backlight unit. Such parameters may include the dimension of the backlight unit, number and location of the lamps, shape of lamp reflector, density or fill factor gradation, pattern of scattering ink dots, and the like. Some parameters may be assigned at fixed values while other parameters may change in its value to achieve an improved optical performance, thus allowing the ray tracing model to determine an improved performance of the backlight unit (i.e., brightness and luminance uniformity).

However, utilizing the ray tracing model 800 based on radiance can be expensive and time-consuming when the number of photons used to simulate the performance of the backlight unit is very large. Therefore, it is desirable to find an optimization method for locating the fewest function evaluations as possible. This can be achieved by directing the tracing model to each pixel in the image and predicting how much light is reflected through each pixel in a two-dimensional environment analysis.

As depicted in FIG. 8, the ray tracing model 800 can be determined using angular space 801, where K is the photometric quantity of the backlight unit and can be determined in radiance in radiometric units or luminance in photometric units. Additionally, the ray tracing model 800 can also be determined using phase space 802, such as a two-dimensional system along a phase plane, or otherwise known as a rectangular system. This phase space 802 allows the ray tracing model 800 to be determined for each two dimensional pixel on the display panel. The relationship between the photometric qualities of the backlight unit of the display panel along the phase space 802 can be determined by modelling or predicting the number of light rays passing through the selected phase-space domains, such as pixels or select rectangular spaces. Thus, an arbitrary bundle of light rays from the backlight unit passing through a given plane (x, y) can be presented as a multiplicity of points in phase space.

Figure 9:
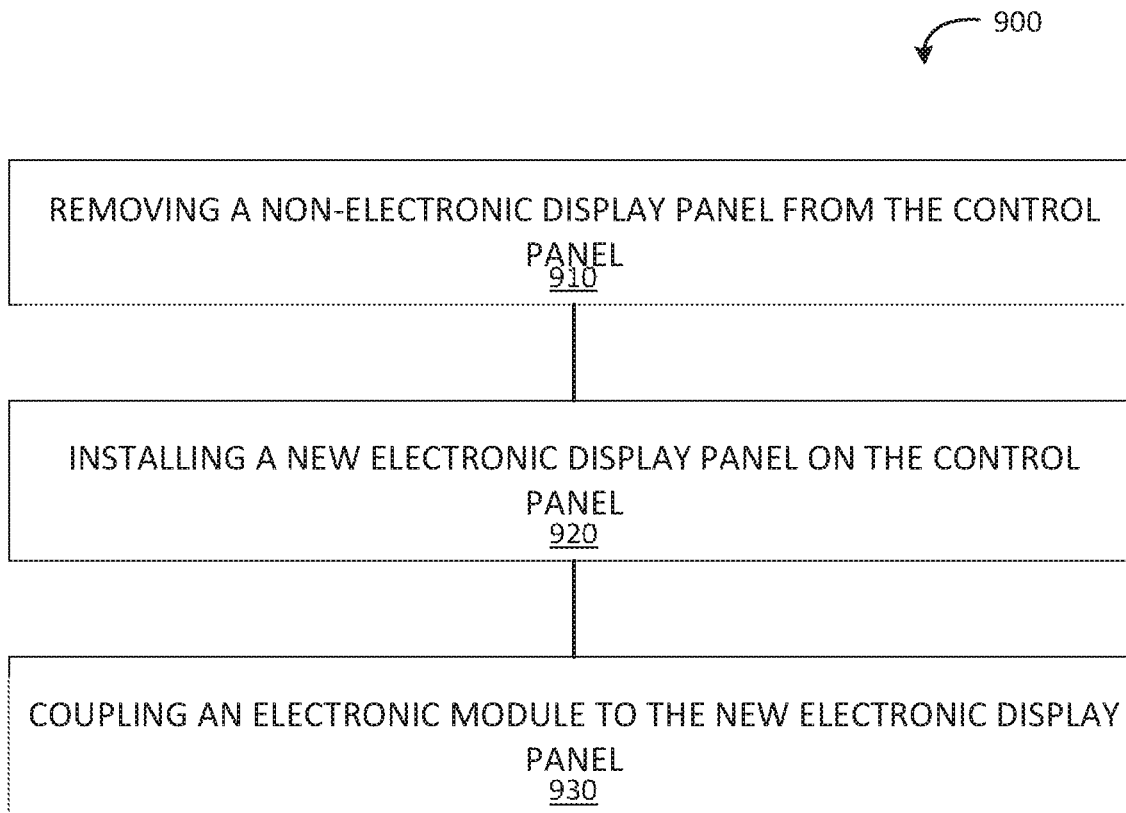
FIG. 9 is a flow chart illustrating a method for installing an updated electronic display panel according to one embodiment.

FIG. 9 is a flow chart illustrating a method 900 for updating a display assembly of a control panel. The method 900 may include removing an analog or non-electronic display panel from the control panel at step 910. The internal wirings within the control panel used with the analog or non-electronic display panel may remain in the control panel.

Next, the method may proceed to step 920, where a new electronic display panel is installed onto the surface of the control panel. Next, the method may proceed to step 930, where an electronic module that was once connected to the non-electronic display panel is now coupled to the new electronic display panel. The new electronic display panel may be installed so that it is aligned with a surface plane of the control panel with the back end of the new electronic display panel connected to the already existent internal wirings of the electronic module. By re-using the internal wirings, the internal wirings within the control panel remain invariant even when replacing an outdated display system for a newer one, such as an electronic display panel. This not only saves costs, but also eliminates complexity and weight associated with the internal wirings.

There may be a new electronic display panel for each electronic module. In other instances, a single electronic display panel may be used to connect with a plurality of electronic modules via the internal wirings in the control panel.

To enhance the illumination of the display panel, where the display panel is a LCD panel, the exemplary process may proceed to operation 930, by modeling a performance of a light source of the display panel to predict a light ray's path and reflectance through pixels on an image plane. In some embodiments, the light ray is a radiance path and its predicted path may be determined in a two dimensional phase space environment.

Figure 10:
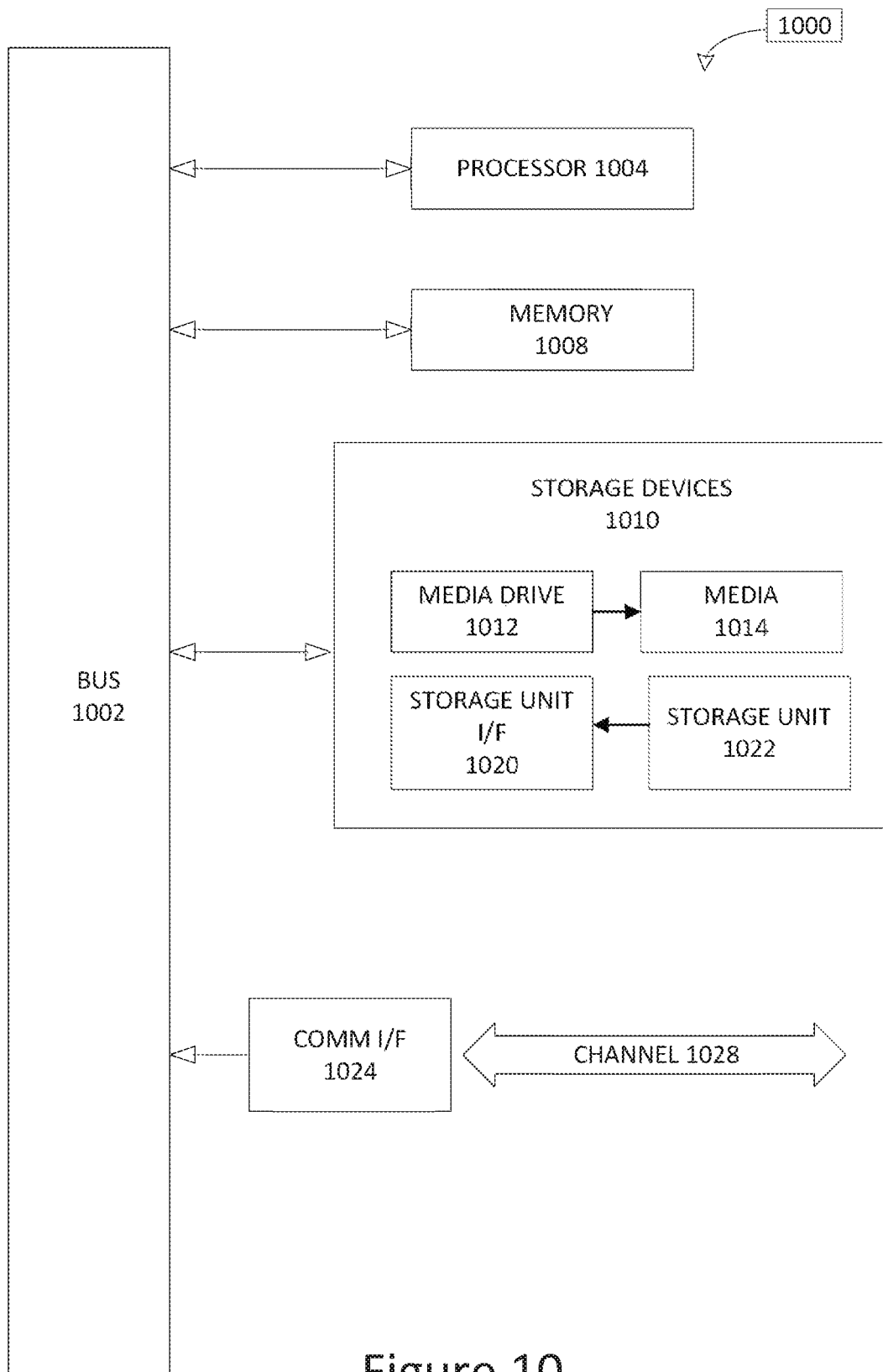
FIG. 10 illustrates an exemplary computer module that may be used when implementing various features of embodiments of the invention.

As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto. One such example computing module is shown in FIG. 10. Various embodiments are described in terms of this example-computing module 1000. After reading this description, it will become apparent to a person skilled in the relevant art how to implement the invention using other computing modules or architectures.

Referring now to FIG. 10, computing module 1000 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 1000 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1000 might include, for example, one or more processors, controllers, control modules, or other processing devices, such as a processor 1004. Processor 1004 might be implemented using a general-purpose or special-purpose processing engine such as, for example, a microprocessor, controller, or other control logic. In the illustrated example, processor 1004 is connected to a bus 1002, although any communication medium can be used to facilitate interaction with other components of computing module 1000 or to communicate externally.

Computing module 1000 might also include one or more memory modules, simply referred to herein as main memory 1008. For example, preferably random access memory (RAM) or other dynamic memory, might be used for storing information and instructions to be executed by processor 1004. Main memory 1008 might also be used for storing temporary variables or other intermediate information during execution of instructions to be executed by processor 1004. Computing module 1000 might likewise include a read only memory ("ROM") or other static storage device coupled to bus 1002 for storing static information and instructions for processor 1004.

The computing module 1000 might also include one or more various forms of information storage mechanism 1010, which might include, for example, a media drive 1012 and a storage unit interface 1020. The media drive 1012 might include a drive or other mechanism to support fixed or removable storage media 1014. For example, a hard disk drive, a floppy disk drive, a magnetic tape drive, an optical disk drive, a CD or DVD drive (R or RW), or other removable or fixed media drive might be provided. Accordingly, storage media 1014 might include, for example, a hard disk, a floppy disk, magnetic tape, cartridge, optical disk, a CD or DVD, or other fixed or removable medium that is read by, written to or accessed by media drive 1012. As these examples illustrate, the storage media 1014 can include a computer usable storage medium having stored therein computer software or data.

In alternative embodiments, information storage mechanism 1010 might include other similar instrumentalities for allowing computer programs or other instructions or data to be loaded into computing module 1000. Such instrumentalities might include, for example, a fixed or removable storage unit 1022 and an interface 1020. Examples of such storage units 1022 and interfaces 1020 can include a program cartridge and cartridge interface, a removable memory (for example, a flash memory or other removable memory module) and memory slot, a PCMCIA slot and card, and other fixed or removable storage units 1022 and interfaces 1020 that allow software and data to be transferred from the storage unit 1022 to computing module 1000.

Computing module 1000 might also include a communications interface 1024. Communications interface 1024 might be used to allow software and data to be transferred between computing module 1000 and external devices. Examples of communications interface 1024 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1024 might typically be carried on signals, which can be electronic, electromagnetic (which includes optical) or other signals capable of being exchanged by a given communications interface 1024. These signals might be provided to communications interface 1024 via a channel 1028. This channel 1028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1008, storage unit 1020, media 1014, and channel 1028. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1000 to perform features or functions of the present invention as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method of updating a display assembly of a control panel comprising:

removing a non-electronic display panel presenting data in an analog format from the control panel by detaching from its internal wirings that connect the non-digital display to an electronic module;

installing an electronic display panel with a front end and a back end onto an area of the control panel where the non-electronic display panel once remained; and coupling an electronic module that was once connected to the non-electronic display panel to the back end of the electronic display panel via the same internal wirings such that digital signals from the electronic module are relayed to the electronic display panel for presenting data in a digital format that was previously presented in an analog format;

wherein the internal wirings of the control panel that are coupled to the electronic module are the same internal wirings that were previously existing in the control panel and were previously attached to the non-electronic display panel, and further wherein the internal wirings utilize both analog signals and digital signals, and remain invariant even when updating the control panel to include the electronic display panel.

2. The method of operating the display assembly of claim 1, wherein the electronic display panel is a liquid crystal display with a backlight unit.

3. The method of operating the display assembly of claim 2, wherein the electronic display panel comprises a collimator to collect light rays from the backlight unit.

4. The method of operating the display assembly of claim 3, wherein the electronic display panel comprises a diffuser to provide a more uniform illumination by minimizing high intensity bright spots.

5. The method of operating the display assembly of claim 4, wherein the display comprises a first focusing lens at a first end of the diffuser and a second focusing lens at a second end of the diffuser.

6. The method of operating the display assembly of claim 5, further comprising modeling a performance of a light source of the electronic display panel to predict a light ray's path and reflectance through pixels on an image plane.

7. The method of operating the display assembly of claim 6, wherein the modeling of the performance of the light source is performed in a two dimensional phase space environment.

8. The method of operating the display assembly of claim 1, wherein the electronic module of one or more electronic assembly units comprises one or more electronic hardware, such that the one or more electronic assembly units may be retrofitted onto the electronic module depending on information to be presented onto the electronic display panel.

9. A method of updating a display assembly of a control panel comprising:

detaching a non-electronic display panel presenting data in an analog format from the control panel;

installing an electronic display panel with a front end and a back end onto a surface of the control panel; and coupling an electronic module that once connected to the non-digital display to the back end of the electronic display panel via the same internal wirings such that digital signals from the electronic module are relayed to the electronic display panel for presenting data for presenting data in a digital format that was previously presented in an analog format;

wherein the internal wirings within the control panel that are coupled to the electronic module are the same internal wirings that were previously existing in the control panel and were previously attached to the non-electronic display panel, and further wherein the internal wirings utilize both analog signals and digital signals, and remain invariant even when updating the control panel to include the electronic display panel.

10. The method of operating the display assembly of claim 9, wherein the electronic display panel is a liquid crystal display with a backlight unit.

11. The method of operating a display assembly of claim 10, wherein the electronic display panel comprises a diffuser to provide a more uniform illumination by minimizing high intensity bright spots.

12. The method of operating the display assembly of claim 9, wherein the electronic module one or more electronic assembly units comprises one or more electronic hardware, such that the one or more electronic assembly units may be retrofitted onto the electronic module depending on information to be presented onto the electronic display panel.

13. The method of operating a display assembly of claim 12, wherein the electronic assembly units comprises at least one of a charge coupled device camera, mission processor unit, loading and storage module, and data transfer module.

14. The method of operating the display assembly of claim 9, wherein the electronic display panel comprises a first focus lens positioned next to a first end of the diffuser and a second focus lens positioned next to a second end of the diffuser to further focus light rays passing through the collimator.

* * * * *